US006643020B2

(12) United States Patent
Mizushima et al.

(10) Patent No.: US 6,643,020 B2
(45) Date of Patent: Nov. 4, 2003

(54) OPTICAL ANALYSIS METHOD FOR INHOMOGENEOUS TURBID MEDIA

(75) Inventors: Yoshihiko Mizushima, Hamamatsu (JP); Kazuji Matsumoto, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 193 days.

(21) Appl. No.: 09/982,022

(22) Filed: Oct. 19, 2001

(65) Prior Publication Data

US 2002/0082504 A1 Jun. 27, 2002

Related U.S. Application Data

(63) Continuation-in-part of application No. PCT/JP00/02638, filed on Apr. 21, 2000.

(30) Foreign Application Priority Data

Apr. 21, 1999 (JP) ..................................... P1999-113708

(51) Int. Cl.$^7$ ........................... G01N 21/00; A61B 5/00
(52) U.S. Cl. ..................... 356/432; 600/310; 600/322
(58) Field of Search ................................ 356/432, 343; 600/310, 322, 473

(56) References Cited

U.S. PATENT DOCUMENTS 5,529,065 A * 6/1996 Tsuchiya ..................... 600/310
6,335,792 B1 * 1/2002 Tsuchiya ..................... 356/432

FOREIGN PATENT DOCUMENTS

| DE | 198 31 424 A1 | 2/2000 |
| JP | 2-234048 | 9/1990 |
| JP | 4-297854 | 10/1992 |
| JP | 6-343625 | 12/1994 |

OTHER PUBLICATIONS

Yukio Ueda et al., "Optical Imaging Reconstruction Using the Average Value as the Reference," Progress in Biomedical Optics, The International Biomedical Optics Society, vol. 2979, 1997, pp. 795–806.

* cited by examiner

Primary Examiner—Frank G. Font
Assistant Examiner—Layla Lauchman
(74) Attorney, Agent, or Firm—Morgan, Lewis & Bockius LLP

(57) ABSTRACT

Light is made incident into an inhomogeneous medium, and transmitted light or reflected light is detected. The intensity of the detected light is represented by the linear sum of exponential functions of penetration depth using e as a base, or a function formed from the exponents and a function derived from the function. This function includes the physical quantity of the inhomogeneous medium as a coefficient. When light amount measurement data are acquired at a plurality of wavelengths or thicknesses, and the light intensity or other known information is substituted into the function and an expression derived from the function, the physical quantity of the inhomogeneous medium can be determined. Thus, an optical analysis method for an inhomogeneous medium, which is capable of accurate analysis, can be provided.

4 Claims, 2 Drawing Sheets

OPTICAL ANALYSIS METHOD FOR INHOMOGENEOUS TURBID MEDIA

RELATED APPLICATION

This is a continuation-in-part application of application serial no. PCT/JP00/02638 filed on Apr. 21, 2000, now pending.

BACKGROUND OF THE INVENTION

1. Field of the Invention

The present invention relate to an optical analysis method for inhomogeneous turbid media.

2. Related Background Art

Probing, measurement, analysis and the like in a medium (substance) using light have been studied. When a medium is irradiated with light, light absorption and scattering occur in the medium. The light absorption and scattering change depending on the physical quantity of each medium constituent material. For this reason, when transmitted light or reflected light from the medium is measured, the physical quantity can be determined on the basis of the measurement value. For example, the light absorption coefficient of a component contained in the medium can be determined on the basis of the measurement value.

Especially, when the medium exhibits not only absorption but also light scattering, the physical quantity is determined in consideration of the scattering coefficient. In a simple case, fundamental expressions are known. Japanese Patent Laid-Open No. 2-234048 discloses a measurement example for a case using a scattering coefficient. In this prior art, the scattering and absorption are analyzed using a time variable on the basis of the transient waveform of a measured light intensity.

Japanese Patent Laid-Open No. 4-297854 is known as a physical quantity analysis example using an exponential function similar to that of the present invention. This prior art discloses a method of correcting an optical diffusion effect in a medium. An exponential function is used as an absorbance correction function.

In a homogeneous medium as well, the effective optical path length increases due to optical diffusion. When the effective optical path length increases, the light intensity attenuates. Hence, in the physical quantity analysis of this prior art, an exponential function having a constant whose physical contents are undefined is empirically introduced in correcting the influence of a change in absorbance, thereby correcting the apparent light intensity. The same phenomenon as described above also occurs in an inhomogeneous medium, though the prior art does not cover any inhomogeneous medium. As described above, in physical quantity analysis for a medium, many methods that take the absorption coefficient and scattering coefficient into consideration are known.

SUMMARY OF THE INVENTION

However, conventionally, when the medium exhibits light scattering and has an inhomogeneous structure, i.e., when the medium is not homogeneous but is buried in a translucent white medium, no physical quantity analysis method therefore is known. Typical inhomogeneous/scattering substances are natural substances and living organisms. The inhomogeneous medium can be approximately regarded as a homogeneous medium and analyzed, as a matter of course. however, when parts have different optical characteristics, and interscattering between the different parts occurs, the degree of light attenuation in the inhomogeneous medium cannot be described by the conventional theory. In addition, since a different refractive index results in a different light speed, an analysis method based on an assumption that light propagates at a predetermined speed cannot be used. Microscopic analysis such as the Monte Carlo method cannot be solved without any precise assumption of inhomogeneous structure distribution and therefore cannot be generally used. As described above, with the conventional method, accurate physical quantity analysis cannot be performed.

It is an object of the present invention to provide an optical analysis method for an inhomogeneous medium, in which, for a medium in an inhomogeneous, polyphase, or mixed state, the components of constituent materials of the medium are separated, and relations to the light intensity are defined, thereby allowing accurate physical quantity analysis for the inhomogeneous medium.

According to the present invention, in an optical analysis method for an inhomogeneous medium, in which light is made incident into an inhomogeneous medium, the intensity of light that emerges from the inhomogeneous medium is detected, the detected light intensity is substituted into a predetermined function, and the physical quantity of the inhomogeneous medium is determined on the basis of the function, solutions of simultaneous differential equations that describe a condition in which light according to light scattering between a plurality of different parts mixes are expressed by a descriptive function. The function is a function that defines the relationship between the light intensity and the linear sum of exponential functions of the penetration depth of the light, which depend on the physical quantity of the inhomogeneous medium and uses e as a base. In this case, the physical quantity of the inhomogeneous medium can be accurately analyzed.

The physical quantity is defined by the absorption coefficient of the inhomogeneous medium, the scattering coefficient of the inhomogeneous medium, or the concentration of a predetermined component in the inhomogeneous medium.

As a characteristic feature, letting I be the intensity, t be the penetration depth, and $\alpha$ and $\beta$ be unknowns depending on the physical quantity, the function is given by $I=(e^{-\alpha t}+e^{-\beta t})/2$.

As a basic characteristic feature, the light that emerges due to reflection is light reflected by the inhomogeneous medium, and the light amount (intensity) of the reflected light is represented by the linear sum of $(\alpha+\beta)/\alpha\beta$ and $1/(\alpha+\beta)$.

DESCRIPTION OF THE PREFERRED EMBODIMENT

An optical analysis method for an inhomogeneous medium according to an embodiment will be described below. In the following description, FIGS. 1A, 1B, and 2 are explicitly shown to help the basic concept.

Figure 1A:
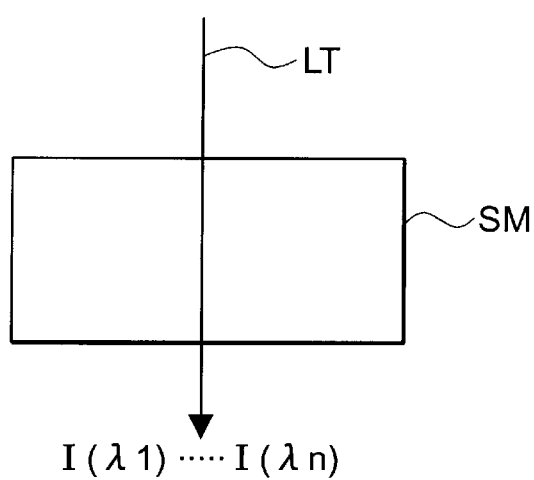
FIG. 1A is a view for explaining intensities $I(\lambda 1), I(\lambda 2), \ldots, I(\lambda n)$ of transmitted light obtained when a sample SM to be measured is irradiated with light LT.
Figure 1B:
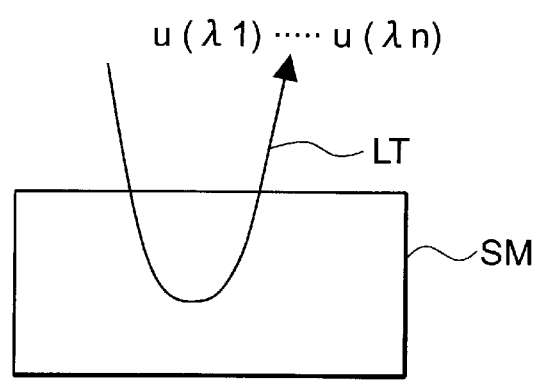
FIG. 1B is a view for explaining intensities $u(\lambda 1), u(\lambda 2), \ldots, u(\lambda n)$ of reflected light obtained when the sample SM to be measured is irradiated with the light LT.

FIG. 1A shows the basic example of transmission and continues spectral intensities I(λ1), I(λ2), ..., I(λn) of transmitted light obtained when a sample SM to be measured is irradiated with light LT. FIG. 1B shows the basic example of reflected light and continuous spectral intensities u(λ1), u(λ2), ..., u(λn) of reflected light obtained when the sample SM to be measured is irradiated with the light LT.

Figure 2:
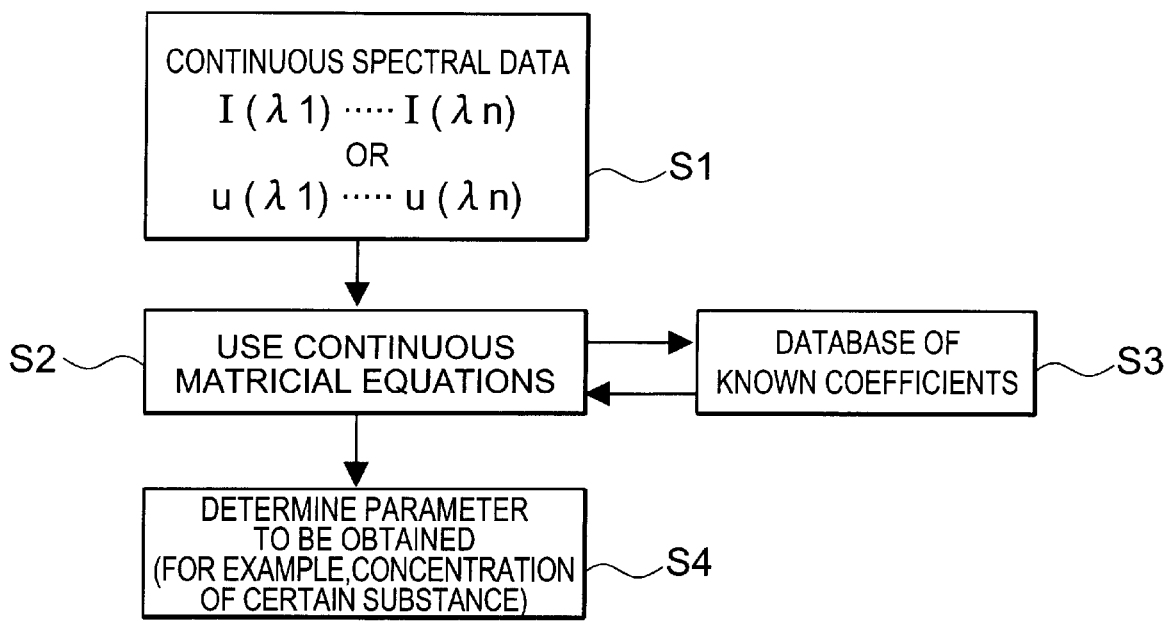
FIG. 2 is a diagram for explaining an inhomogeneous medium analysis method according to the embodiment.

FIG. 2 is a diagram for explaining an inhomogeneous medium analysis method according to the embodiment. In this embodiment, first, the continues spectral data I(λ1), I(λ2), ..., I(λn), and u(λ1), u(λ2), ..., u(λn) are obtained, as described above (S1). Simultaneous matricial equations (simultaneous equations) are made from the obtained data (S2). As these equations, those to be described later are used. As parameters used in the equations, parameters in a known coefficient database (S3) are used, or after measurement calculation, the values in the known coefficient database may be changed and obtained. Finally, the final parameters (e.g., the concentration of a specific substance) are determined (S4). The outline has been described above in accordance with the drawings and the like. The optical analysis method for an inhomogeneous medium according to the embodiment will be described below.

First, the general light absorption and scattering phenomena in a homogeneous medium will be described.

Generally, light absorption and scattering occur in a medium. In the following description, $\mu_a$, $\mu_s$, x, t, and P are defined as follows.

TABLE 1

| |
|---|
| $\mu_a$: Absorption coefficient per unit molar concentration of the medium |
| $\mu_s$: Scattering coefficient per unit molar concentration of the medium |
| x: Light intensity |
| t: Penetration depth of light |
| P: Existent molar concentration of the medium |

When absorption and scattering coexist, since the two events are independent, the following differential equation (equation 1) is obtained as a satisfactory approximation, and its solution is given by (equation 2).

$$\frac{dx}{dt} = -(\mu_a + \mu_s)Px \quad \text{(equation 1)}$$

$$x = e^{-(\mu_a + \mu_s)Pt} \quad \text{(equation 2)}$$

The scattering phenomenon may have anisotropy. If the anisotropy is taken into consideration, $\mu_s'$ given by (equation 3) is used in place of the scattering coefficient $\mu_s$. In this case, g is the anisotropy factor which is 0 for isotropic scattering, +1 for only forward scattering, and −1 for only backscattering.

$$\mu_s' = \mu_s(1-g) \quad \text{(equation 3)}$$

When three of the penetration depth t, absorption coefficient $\mu_a$ and scattering coefficient $\mu_s$ of the medium, and the existent molar concentration P of the medium are known, and in this state, the light intensity x is measured, the remaining value can be specified from (equation 2).

However, the above method is a physical quantity measurement algorithm that is made on an assumption that the medium is homogeneous. A more accurate algorithm is required to measure or analyze a physical quantity in an inhomogeneous medium. Measurement and analysis of a physical quantity in an inhomogeneous medium will be described below.

The following description will be done assuming that the medium is an inhomogeneous medium. In simple case, assume that two parts X and Y are present in the propagation direction of light. When the medium is a living tissue, the part X represents of blood capillaries, and the part Y represents a tissue (fat or flesh) other than the blood vessels. These parts are mixed.

Interaction occurs between the part X and the part Y as the light travels, and light mixing occurs. The light is re-distributed between the two parts due to scattering of light. In the following description, x and y are defined as follows.

TABLE 2

| |
|---|
| x: light intensity (light amount) in the part X |
| y: light intensity (light amount) in the part Y |

More exactly, for the total sectional area of a light beam probe to be measured, x or y corresponds to the number of photons present in a volume defined by the product of the total sectional area of the part X or Y contained therein and the unit depth. Alternatively, x or y may be regarded as a value obtained by multiplying the photon density by the sectional area of the part X or Y. Since the values x and y are erased later, the density or sectional area need not be specified here.

The light intensities (light amounts) x and y in the parts X and Y are given by the following differential equations (equations 4).

$$\frac{dx}{dt} = -ax + by \quad \text{(equations 4)}$$

$$\frac{dy}{dt} = cx - dy$$

Coefficients a, b, c, and d are defined as follows.

TABLE 3

| |
|---|
| a: Loss coefficient by absorption and scattering in the part X |
| b: Coefficient of a component of scattered light in the part Y, which mixes into the part X |
| c: Coefficient of a component of scattered light in the part X, which mixes into the part Y |
| d: Loss coefficient by absorption and scattering in the part Y |

The absorption, scattering, and loss will be described. For a more detailed discussion, $\mu_a$ and $\mu_s$ will be more accurately defined below.

In the description, $\mu_a$, $\mu_s$, $\mu_{ax}$, $\mu_{sx}$, $\mu_{ay}$, $\mu_{sy}$, $\mu_s''$, E, $P_x$, and $P_y$ represent the following coefficients.

TABLE 4

| |
|---|
| g: Anisotropic factor |
| $\mu_a$: Absorption coefficient per unit length per unit concentration |
| $\mu_s$: Scattering coefficient per unit length per unit concentration |
| $\mu_{ax}$: Absorption coefficient per unit length per unit concentration in the part X |
| $\mu_{sx}$: Scattering coefficient per unit length per unit concentration in the part X |

TABLE 4-continued $\mu_{ay}$: Absorption coefficient per unit length per unit concentration in the part Y
$\mu_{sy}$: Scattering coefficient per unit length per unit concentration in the part Y
$\mu_s''$: Light scattering coefficient per unit length per unit concentration in the horizontal direction
E: Geometrical structural coefficient of the mutual exchange across the boundary plane light enters the adjacent part
$P_x$: Concentration of the target substance in the part X
$P_y$: Concentration of the target substance in the part Y The optical loss coefficient to another part is given by the product $\mu_s'' \times E$ of the horizontal light scattering coefficient $\mu_s''$ and structural coefficient E. The horizontal light scattering coefficient $\mu_s''$ is approximated to $\mu_s''=\mu_s$. The horizontal light scattering coefficient $\mu_s''$ defines a condition in which the light travels from the part X to the part Y or from the part Y to the part X.

When the absorption coefficient coexists with the scattering coefficient, the mean free path of photons is related to the sum of the absorption coefficient and scattering coefficient. That is, $$b \propto \frac{\mu_{sy}}{\mu_{ay} + \mu_{sy}}$$

$$c \propto \frac{\mu_{sx}}{\mu_{ax} + \mu_{sx}}$$

If the scattering coefficient is large, or the sectional area of one part is smaller, b (coefficient of a component in scattered light in the part Y, which mixes into the part X)=c (coefficient of a component in scattered light in the part X, which mixes into the part Y).

In a living body, since scattering is much larger than absorption, b=c holds. These are constants independent of a wavelength. This is very effective in simplifying the calculation. The reason is as follows. When light should mix into an adjacent part, photons must be present within the mean free path for the boundary surface. However, the mean free path is inversely proportional to the scattering substance concentration.

When the above coefficients $\mu_{ax}, \mu_{sx}, \mu_{ay}, \mu_{sy}, \mu_s'', E_x, E_y, P_x,$ and $P_y$ are used, the coefficients $\underline{a}$, b, c, and d are given by (equations 5). Note that b and c are added independently of $\underline{a}$ and d. The suffices x and y represent that the coefficients are related to the parts X and Y.

$a=(\mu_{ax}+\mu_{sx}(1-g)+\mu_{sx}E_x)P_x$
$b=\mu_{sy}E_yP_y$
$c=\mu_{sx}E_xP_x$
$d=(\mu_{ay}+\mu_{xy}(1-g)+\mu_{sy}E_y)P_y$

As described above, assume that an excess epidermal layer, e.g., a skin is present except the target medium (tissue), and the target medium is to be measured through the skin. In this case, the position at which the light that has transmitted through the skin becomes incident on the internal tissue is defined as t=0. The attenuation amount of light transmitted through the skin is defined as $K^*$. If absorption or scattering on the skin is independently measured, $K^*$ can be specified, and the resultant measurement value can be corrected by $K^*$.

As is self-evident, the correction by $K^*$ is applied every time as needed. In addition, since $K^*$ can be processed as an unknown coefficient, as will be described later, this correction will be omitted in the following function expression.

In the following description, the measured light amount will be standardized with reference to the incident light amount at t=0. The general solutions of the above simultaneous differential equations (equations 4) are given by:

$$x=Ae^{-\alpha t}+Be^{-\beta t}$$

$$y=Ce^{-\alpha t}+De^{-\beta t} \quad \text{(equations 6)}$$

In examining the equations, if the section of each part is much larger than that of the measurement light probe, only the homogeneous phase of the part X or Y can be selected and irradiated with the light, and therefore, the problem can be made simple.

However, in fact, the sectional area of each part is often much smaller than the sectional area of the probe, and the actually measured light amount I is always the sum of the light amounts x and y. In other words, practically, only the light amount I (=x+y) is a significant measurable quantity.

Additionally, in such a case, the light amount I to be measured contains the influence of both the parts X and Y, and the light of parts interact to each other. Hence, when the scattering is strong, the light amounts are averaged between the parts (tissues).

As an initial condition at the time of light incidence, the incident light amount when t=0 is standardized by $$I=x+y=1 \quad \text{(equation 7)}$$

The light amount I at the depth t is given by $$I=x+y=(A+C)e^{-\alpha t}+(B+D)e^{-\beta t} \quad \text{(equation 8)}$$

By standardization by (equation 7), (equation 8) yields $$I = x + y = \frac{e^{-\alpha t} + e^{-\beta t}}{2} \quad \text{(equation 9)}$$

That is, the output light amount I (=x+y) can be standardized only by $\alpha$ and $\beta$. This is different from the single exponential function expression for a homogeneous phase, as indicated here.

A theorem related to various coefficients will be derived from some arithmetic operations. The values $\alpha$, $\beta$, $\alpha+\beta$, $\alpha-\beta$, and $\alpha\beta$ are given by $$\alpha = \frac{(a+d) + \sqrt{(a-d)^2 + 4bc}}{2} \quad \text{(equations 10)}$$

$$\beta = \frac{(a+d) - \sqrt{(a-d)^2 + 4bc}}{2}$$

$$\alpha + \beta = a + d$$

$$\alpha - \beta = \sqrt{(a-d)^2 + 4bc}$$

$$\alpha\beta = ad - bc$$

Useful expressions including no penetration depth t of light can also be used as a theorem. Of the coefficients $\underline{a}$ and b, components that do not escape to other tissues are defined as m and n, which are given by $$m=a-c$$

$$n=d-b \quad \text{(equations 11)}$$

Hence, (equation 12) also holds.

$$b - c = \frac{m^2 + n^2 + 2\alpha\beta - (\alpha + \beta)(m + n)}{m - n} \quad \text{(equation 12)}$$

When b=c, m, n, $\alpha$, and $\beta$ satisfy $$m^2+n^2+2\alpha\beta-(\alpha+\beta)(m+n)=0 \quad \text{(equation 13)}$$

When the light amount I is measured, unknowns are $\alpha$ and $\mu$. If the number of equations are two, including (equation 9),$\alpha$ and $\beta$ can be specified. The additional equation can be obtained by knowing, e.g., the penetration depth t of light.

When $\alpha$ and $\beta$ are specified, physical quantities related to the target inhomogeneous medium can be specified. In other words, all pieces of information are acquired even for the inhomogeneous medium on the basis of the above equations.

Examples of the physical quantities are the absorption coefficient, scattering coefficient, structural coefficient, and target substance concentration ($\mu_{ax}$, $\mu_{sx}$, $\mu_{ay}$, $\mu_{sy}$, $E_x$, $E_y$, $P_x$ and $P_y$) for defining the coefficients a, b, c, and d that form $\alpha$ and $\beta$. If the number of equations obtained from experiments is equal to or larger than the number of unknowns, various physical quantities can be specified.

Generally, since b≠c, b and c are handled as undefined coefficients and added to the concentrations $P_x$ and $P_y$ to be obtained, thereby solving the simultaneous equations. Since the number of unknowns is large, measurements are repeated at various wavelengths, and resultant equations are composed into simultaneous equations, and a set of optimized solutions is obtained.

As a characteristic feature of this analysis method, the solutions can be obtained independently of the values b and c because characteristics such as the structure of inhomogeneous system and the interaction are erased without being positively expressed. In addition, no approximation is mathematically included, and strict solution expressions can be held. Hence, the solutions can be derived without considering the inhomogeneous state. That is, this method can be applied even when the degree or sectional area of each part varies in the propagation direction of light. This is because the structure and characteristic features (b and c) of the inhomogeneous system are eventually erased without any constraint conditions.

As described above, according to the above method, $\mu_a$ and $\mu_s$ unique to each part are the standard values of absorption and scattering coefficients per unit molar concentration. Hence, when the determined $\alpha$ and $\beta$ are combined with the above theorems, the unknowns, e.g., $P_x$ and $P_y$ at each wavelength can be determined.

When the same method as described above is repeated while changing the wavelength of incident light in order to increase the number of equations, the absorption spectrum within a desired wavelength range can be obtained. When a plurality of components are assumed, the obtained absorption spectrum is the sum of absorption coefficients of those components and therefore must be separated. The absorption spectrum of each single component is normally known from references and the like. For this reason, the concentrations of the respective components can be separated and determined by linear programming of several variables using the spectra of the components as known coefficients.

Various methods can be used for actual measurement. For example, if measurement can be done while changing the thickness of the sample to be measured at several points, the transmission output light amount is expressed as a function of thickness, and $\alpha$ and $\beta$ are determined such that the function of thickness is represented by the linear sum of two exponential functions. This calculation is easy because no other undefined coefficients are present.

In determining the above-described unknowns, to obtain a number of equations equal to or larger than the number of unknowns, measurements must be performed under various measurement conditions. One of the variable parameters is, e.g., the thickness t. However, some samples cannot change the thickness t. Assume that the thickness t cannot be changed in measuring the transmission light amount I. At this time, since $\alpha$ and $\beta$ cannot be directly determined, measurements are performed in the whole spectrum region. With this process, the number of equations can be increased. First, assume that the spectrum per unit mole of each single component is known. In this case, for each at each wavelength, to determine the existent amount of each component, calculations given by (equation 9) and the theorems (e.g., (equations 10)) are performed. When $\alpha$ and $\beta$ are numerically converged by optimum calculation combined with the above calculations, the solutions can always be obtained.

When unknowns are $\alpha$, $\beta$, and t, at least three wavelengths are necessary for the measurement, and preferably, a larger number of wavelengths are used for the measurement to reduce the number of errors. The subsequent method is the same as described above. Instead of $\alpha$ and $\beta$, $P_x$ and $P_y$ to be obtained at the next stage may be directly used. To separate a plurality of substances, the number of wavelength measurement points are preferably larger. In addition, since matrix calculation is performed, to decrease the number of errors, the number of processes of calculation is preferably decreased by directly calculating $P_x$ and $P_y$.

Another example for no changeable thickness t or not related to a specific thickness is a reflection method. In this method, since light incident into the substance to be examined returns to the incident surface due to the internal scattering, the light is measured to analyze the internal information. As an application to a homogeneous phase, the Kubelka-Munk (K-M) method is often used. However, the conventional K-M method is supposed to be inapplicable to an inhomogeneous phase. A calculation method for such a case will be described here.

Using the standardized coefficients, the intensity (u) of reflected light, i.e., returned light is given by $$u = \mu_{SK}L \times \frac{1 - \mu_{SK}L}{2} \text{ for} \quad \text{(equation 14)}$$

$$L = \frac{\frac{\alpha+\beta}{2\alpha\beta} + \frac{2}{\alpha+\beta}}{4}$$

$$bc = \frac{8Lad(a+d) - (a^2 + 18ad + d^2)}{8\{L(a+d) - 2\}}$$

Originally, L implies the optical mean free path in the forward propagation. In the K-M method, however, the backward propagation is treated in the theory, where the normalized backward flux has an effective backward mean free path.

In this case, $\mu_{SK}$ is the reverse (back) scattering coefficient and can be expressed by $\mu_{SK}=\mu_s g$. In the present invention, this is a number averaged for the parts X and Y. If this value is known, it is used as a known coefficient. If this value is unknown, it can also be handled as an undefined coefficient in the optimum value calculation (to be described later).

If unknowns are $\alpha$, $\beta$, and $\mu_{SK}$, measurements are performed using at least three wavelengths, or if possible, a larger number of wavelengths to decrease the number of errors. Instead of $\alpha$ and $\beta$, $P_x$ and $P_y$ to be obtained at the next stage may be directly used as unknowns.

In the reflection method, since the interactive terms are included as non-linear expressions, the equations cannot be analytically solved to the last. However, as has already been described above, using the fact that b and c are constants irrelevant to wavelengths, and the spectra for all wavelengths are measured, and the spectrum of each single component is known for each wavelength, the equations can be solved by numerical calculation while regarding the formulation ratio of the components as an undefined coefficient. Since linear programming (least square method) of several variables including undefined coefficients is known, convergent solutions can be obtained by a computer under this condition.

Processing executed when two parts X and Y are present has been exemplified above. At this time, two parameters $\alpha$ and $\beta$ are used, as described above. If three parts X, Y, and Z are present, processing starts from a matrix of three variables, and parameters $\alpha$, $\beta$, and $\gamma$ are used.

If a plurality of types of target analysis substances are contained, and the spectra overlap at the same wavelength, the spectra must be separated. This can be regarded that the above-described $P_x$ and $P_y$ contain a plurality of components, and the respective linear sums contribute. Hence, the equations can be solved by increasing the number of measurement wavelengths in accordance with the increase in numbers of unknowns and undefined coefficients. That is, in this method, measurements must always be simultaneously executed using several (at least three) wavelengths, and more preferably, 10 or more wavelengths.

Another application form will be described. It is important for practical use to apply the method to another analysis method when one part contains a plurality of target substances. In this example, substances i and j coexist in the part X, and another scattering substance k is present in the part Y, though the substance k is not the target substance. When the concentrations are defined as $P_i$, $P_j$, and $P_k$ and coefficients $\beta$ are identified by suffices i, j, and k, equations corresponding to (equations 4) and (equations 5) are given by $$\frac{\partial x}{\partial t} = -(\mu_a + \mu_s')_i P_i x - (\mu_a + \mu_s')_j P_j x + \mu_{sk}'' P_k y \quad \text{(equations 15)}$$

$$\frac{\partial y}{\partial t} = -(\mu_{si}'' + P_i + \mu_{sj}'' P_j)x - (\mu_a + \mu_s')_k P_k y$$

For the sake of simplicity, when $(\mu_a + \mu_s')_l$ is rewritten as $\beta_l$, the equations and arithmetic operations can be contracted by $$\frac{\partial x}{\partial t} = -ax + by \quad \text{(equations 16)}$$

$$\frac{\partial y}{\partial t} = cx - dy$$

$$a = \mu_i P_i + \mu_j P_k$$

$$d = \mu_k P_k$$

If unknown amounts are $P_i$ and $P_j$ and undefined coefficients are b and c, the solutions can be obtained using at least four wavelength measurement values.

The expression for it is long and will be omitted here. Preferably, optimum calculation is applied using a larger number of wavelengths to minimize the number of errors, as a matter of course.

As has already been described above, when scattering is strong, or for blood capillaries, the coefficients for interscattering are equal. If the coefficients are defined as a common value e, the equations can be rewritten to $$\mu_{sk}'' P_k = \mu_{si}'' P_i + \mu_{sj}'' P_j = e \quad \text{(equation 17)}$$

For the sake of simplicity, if the total value of the substances i and j is constant ($P_0$), and the ratio of the substance i is represented by a saturation (S), S is given by $$P_i + P_j = P_0 \quad \text{(equations 18)}$$

$$S = \frac{P_i}{P_0}$$

Hence, the above equations are simplified to $$\frac{\partial x}{\partial t} = -[(\mu_i - \mu_j)S + \mu_j]P_0 x + by \quad \text{(equations 19)}$$

$$\frac{\partial y}{\partial t} = cx - \mu_k P_k y$$

To solve these equations, arithmetic operations are performed while executing measurements using a plurality of wavelengths, as already described above. A description will be made to help understanding the condition. Approximate expansion for the combination of the above equations and (equation 9) yields $$x+y=(\frac{1}{2})\times\exp[(-\frac{1}{2})\{(\mu_i-\mu_j)S+\mu_j+\mu_k P_k\}t]\times[1+(t^2/8)\times[\{(\mu_i-\mu_j)S+\mu_j-\mu_k P_k\}^2+4\,bc]] \quad \text{(equation 20)}$$

The right-hand side is approximated by a straight line off the origin while plotting S along the abscissa. This typically indicates that the method of the present invention is different for a simple exponential function for a homogeneous phase.

For the K-M method as well, the intensity u is measured at a plurality of wavelengths, and the equations can be combined and solved. The solution expression is long and will be omitted here.

As described above, even when a plurality of substances coexist in one part, the solutions can always be obtained by calculating corresponding simultaneous equations. In the above example, $P_i + P_j = P_0$, holds. However, the present invention is not limited to this. Measurements are executed at wavelength points necessary for obtaining simultaneous equations necessary for solving the unknowns.

To obtain solutions that minimize the number of errors in the whole wavelength range is a means of linear programming. This greatly improves the accuracy. Since the interactive terms are erased, the wavelength dependence of interscattering causes no error. Another means for omitting labor for measurements will be described.

In the above measurement, a comparison standard can be made only once by another means and used. With this method, changes in value S can be traced every time measurement is performed at the same wavelength.

As a characteristic feature of this method, once the comparison standard is determined, measurement of every time can be largely simplified by storing the determined value. This is because the characteristic of the inhomogeneous structure is erased by arithmetic operation and is a characteristic feature of this patent, which is obtained by the principle of the function expression. Only by adding some arithmetic operations, the target calculation can be achieved, as for a homogeneous phase.

Still another application will be described. The above-described methods are applied to a temporally steady state.

However, this patent is not limited to this and can also be applied to a temporally changeable state. For a normal object, the time until the light amount distribution reaches the equilibrium state is on the order of μsec or less because the light traveling time from the incident end to the exit end becomes longer than a simple traveling time due to the influence of multiple scattering. Hence, a case of an especially high speed corresponds to analysis of high-speed combustion reaction, explosion, or fracture phenomenon. When the speed in the object is actually low, and the light source itself emits modulated light, the method can be applied to any cases.

For a time ($\tau$) dependence term in (equations 4), (equations 21) hold.

$$\frac{\partial^2 x}{\partial t \partial \tau} = -\left(a\frac{\partial x}{\partial \tau} + \frac{\partial a}{\partial \tau}x\right) + b\frac{\partial y}{\partial \tau}$$

$$\frac{\partial^2 y}{\partial t \partial \tau} = c\frac{\partial x}{\partial \tau} - \left(d\frac{\partial y}{\partial \tau} + \frac{\partial d}{\partial \tau}y\right)$$

(equations 21)

The parenthesized second term on the right-hand side corresponds to a case wherein the absorption/scattering coefficient or concentration varies. The b and c terms are almost constant, as already described above.

A case of modulated light be described. When the temporal change in each substance physical quantity is slow, if $\partial a/\partial \tau$ and $\partial d/\partial \tau$ are neglected, the above equations are rewritten, using $\partial x/\partial \tau = x''$ and $\partial y/\partial \tau = y''$, to $$\frac{\partial x'}{\partial t} = -ax' + by'$$

$$\frac{\partial y'}{\partial t} = cx' - dy'$$

(equations 22)

and can be similarly solved.

When modulated light is used, the measurement sensitivity in the detection system can be increased using a means such as synchronous detection, and the present invention can also be applied to these applications.

A case of high-speed reaction will be described next. For the sake of simplicity, a variable element is assumed to be a, and (equations 23) hold.

$$\frac{\partial x'}{\partial t} = -ax' + by' - \frac{\partial a}{\partial \tau}\int x' d\tau$$

$$\frac{\partial y'}{\partial t} = cx' - dy'$$

(equations 23)

Generally, this can be handled as perturbation. That is, once the solution of a canonical equation is obtained, calculations can be repeatedly performed using the solution as an initial value such that $(\partial a/\partial \tau) \int x' d\tau$ is optimized, and the reaction parameter $\partial a/\partial \tau$ to be obtained is determined.

To increase the calculation accuracy, wavelength spectrum data is used as needed, as described above.

The analysis method described here is very effective for practical use because even when a plurality of parts x and y have a difference in detailed optical characteristic, e.g., a difference in refractive index, the target solution can be obtained without positively handling the difference. For example, since a heart pulsation condition can be extracted by the optical characteristic measurement, information related to blood circulation can be obtained. In a synthetic organic factory, even when a fluidized solution in a reactive container or pipe is an inhomogeneous mixed solution, the fluid condition can be monitored. These techniques are also incorporated in this patent.

As a detailed example, a measurement example for a living body will be described. For example, the oxygen concentration in blood is represented by the concentrations of oxyhemoglobin and reduced hemoglobin. This method can also be applied to quantitative concentration measurements for glucose, red blood cells, cholesterol, neutral lipid, and the like and therefore can replace the conventional blood examination using sampled blood. The absorption spectra of these components are well known and range from the visible to infrared regions.

When these components are present in blood, the absorption coefficient and scattering coefficient are supposed to act in the medium as a linear sum.

In an actual living body, blood vessels and other tissues are present in an inhomogeneous polyphase mixed state. This poses two problems: scattered light mixes into other tissues, and even when the spectra can be separately measured, they are only qualitatively detected, and the absolute values are undefined.

To solve these problems, another method such as a pulse oxymeter was being conventionally used, since only with normal spectral curve, no absolute value could be taken till now.

A new embodiment for solving the problems only by transmission (or reflection) of light will be described. For (equations 4), assume that the part X is the blood portion in blood vessels, the part Y is a tissue portion other than the blood portion, and x and y are light amounts contained in these parts, respectively.

The light is exchanged between the part X and the part Y due to diffusion and the like. As a characteristic feature, the accurate structure and the function form of light exchange are need not be accurately described because the accurate structure and the function form are erased by calculation process.

In this embodiment, since the light is made incident through another surface layer such as a skin, the absorption coefficient and the like in the skin layer must be newly taken into consideration. To do this, the attenuation amount $K^*$ at each wavelength in the skin layer is also measured or expected as a known coefficient in advance for the measurement portion, and a loss by attenuation is independently corrected. Alternatively, when the attenuation amount is handled as an undefined coefficient, the calculation can be avoided.

The measurement light is emitted from the light source into the living body through an optical fiber and wavelength filter. The irradiant and receiver probes are combined together in a common bundle of optical fibers. Light from a wide area of, e.g., about 1 cm$^2$ can be received such that the sum of outputs from the part x and part y can be measured.

In the first measurement, a white plate is irradiated with the light, and reflected light is received to determine the reference value of standardized light amount. When the light is intermitted at a predetermined period as needed, and synchronous detection is performed on the light-receiving side, the signal-to-noise ratio can be improved.

If it is necessary, the oxygen saturation or the like may be measured by another method only in the first case and used as a comparison standard to simplify the arithmetic operations, though it is not essential.

In the actual measurement, the measurement probe is preferably applied to a single place for measurements at a plurality of predetermined wavelengths. Since it guarantees that the interactive terms are common, the arithmetic accuracy and the like become high, though it is not essential because the interactive terms can be erased for each wavelength.

The output light amounts are measured for each wavelength. The results are formed into a data list as standardized numbers and stored in a storage device. The wavelength measurement is performed for a plurality of wavelengths. For accurate measurement, the wavelength range is preferably, e.g., 450 to 1,500 nm, i.e., from the visible range to the near-infrared range.

The absorption spectra within the wavelength range are acquired in the above way. To determine the concentrations $P_x$, and $P_y$ at each wavelength from the plurality of measurement values using the above method, the simulated spectra are calculated by the least square method with reference to the known absorption spectrum of oxyhemoglobin, hemoglobin, cytochrome, or the like, thereby obtaining the concentrations $P_x$ and $P_y$.

When one absorption spectrum apparently corresponds to a single absorption substance, the concentration can be obtained because the standard value of the absorption coefficient itself is known. However, generally, a value at a certain wavelength is probably the sum of absorptions of a plurality of components, they must be separated. As described above, the components can be separated on the basis of the spectrum profile of the measurement data. Hence, after that, each peak value is compared with the absorption coefficient to be expected.

For this purpose, calculation is performed in the following way. The spectra of the light absorbing materials can be expected in advance. For, e.g., a human body, the tissues include cytochrome, reduced hemoglobin and oxyhemoglobin. The light absorption coefficients and scattering coefficients of the components in the homogeneous phase are known and stored in a storage device as a database. The matrix elements for linear programming are determined using these data as reference data and used for the subsequent calculation.

As a general method, an optimizing method for a nonlinear function is used. That is, a Gauss-Newton expression holds between the deviation vector of an unknown and the vector of the measurement value at each wavelength $\lambda$. A deviation equation from the initial value to the true value is given by $$(\Delta z)_\lambda = (J)(\Delta p)$$

or $$(\Delta p) = J^{-1}(\Delta z)_\lambda \qquad \text{(equation 24)}$$

where z is the vector of the measured light amount for each wavelength, $\Delta p$ is the vector of the concentration of the unknown to be obtained, and J is the Jacobian matrix having rows of unknowns and columns of measurement points. In accordance with the function of z, differential coefficients are calculated for each combination. To form an inverse matrix, when a transposed matrix $J_t$ is used, $J^{-1} = (J^tJ)^{-1}J^t$, and the deviation of a new unknown can be calculated. Hence, approximation can be sequentially performed toward the true value.

In either the transmission method or the K-M method, since the light amount is analytically expressed, all the elements of the Jacobian matrix can be analytically handled as they are differential coefficients between the vectors. For this reason, the differential elements of each matrix element can also be analytically expressed and calculated. This is the remarkable characteristic feature of this method.

In each part, analysis can be executed by regarding that the absorption of each component forms a linear sum. Interscattering between the parts X and Y is processed as an undefined coefficient, as needed.

The obtained result is the linear sum of the absorption coefficients of the constituent substances in each part and therefore can be solved by linear programming. At this time as well, the accuracy can be increased using the least square method for all measurement wavelengths.

As described above, since a number of simultaneous equations can be formed for a number of measurement wavelength values, as needed, and simultaneous equations larger in number than the unknowns can be prepared, processing can be executed even with an undefined coefficient.

After the absorption coefficients for each part are obtained at each wavelength, since individual absorption spectra are known, linear programming is used to search each component ratio such that the standard waveform data matches the concentration measurement value of each component. To solve and optimize the inverse matrix, a computer having a known numerical calculation program is caused to execute the calculation. Since the number of rows and the number of columns do not match, the inverse matrix calculation must be combined with the transposed matrix.

To increase the calculation accuracy, the background is preferably taken into consideration as an undefined coefficient. A portion that remains as a calculation error is generated by stray light and light scattering and generally monotonically changes with respect to the wavelength. Especially, since the main composition in a homogeneous phase is generally known depending on the medium, the background can easily be determined and subtracted.

Under the above constraint conditions, each component can be analyzed by the nonlinear optimizing method of several variables, and an optimum solution can be approximately converged to subsequently obtain the unknown for the target component. At this time, an almost expected value t may be used as the start value for high-speed convergence.

In this theory, note a case wherein parameters such as the penetration depth t or interactions b and c are included or a case wherein the parameters cannot be determined in advance. For example, the transmission thickness t is at a position separated from the light incident point of the object to be measured. However, when the light emerges from the same surface as the light incident surface and is measured, the principal ray path is not linear but is considerably bent, and the representative value t cannot be determined. In such a case, the method of assuming the average value t in advance should not be used because attenuation is represented by an exponential function with respect to the path length, the ray path is complex, and especially for an inhomogeneous structure, the principal ray determination by the Monte Carlo method is also uncertain, and a large error is generated.

In this case, by handling the parameters as undefined coefficients, the most probable $\alpha$ and $\beta$ can be determined. In addition, as described in the above section, using the fact that the spectrum of the actual measurement value can be decomposed into expected components, $P_x$ and $P_y$ can be defined such that they match the most probable component values.

Alternatively, calculation may be done using the fact that the theory has analytic expression. At multiple wavelength points, the expression of z and various theorems above are combined to erase the interactive terms b and c, and solutions for ($\alpha$, $\beta$) or (a, d) are obtained. These values are represented by linear sums of absorption coefficients of the constituent substances in each part and therefore can be solved by linear programming. At this time as well, the accuracy can be increased using the least square method for all measurement wavelengths.

As described above, as the essence of the method of the present invention, the light amount can be described by a function derived from linear combination of two exponential functions using $\alpha$ and $\beta$ as power exponents and the exponents, and analytic expression is used by combining the functions. The optical constant of the medium which is inhomogeneous and exhibits strong scattering can be expressed through this expression. In addition, the undefined factors such as the structure related to the inhomogeneous medium need not be positively handled.

When numerical values are calculated using the basic equations of the present invention, application of a known coefficient such as an absorption coefficient or scattering coefficient, and solution by assuming an undefined coefficient can be appropriately done in accordance with the convenience for calculation. To derive an optimum value by linear programming is also a known mathematical means.

As has been described above, that the measurement and analysis can be performed for an inhomogeneous medium without positively handling the inhomogeneous state has an important value for practical use, and several examples thereof have already been described.

Objects in a living body, plant, leaf, fruit, wood, powder, mixture of solid and liquid materials, emulsion, soil water, seawater, or vapor have a strong scattering characteristic as well as heterogeneity, and many errors occur in optical measurement of the objects, which is important for practical use. Since these inhomogeneous internal tissue structures exhibit various complex conditions, measurement can rarely be executed while specifying each of these conditions. The method of the present invention proposes a mathematical method of obtaining a result without positively handling the complex elements.

The essence is based on the fact that a solution can be expressed by linear combination of two exponential functions, and a finding that the solution can be obtained in consideration of the heterogeneity. For a detailed application of the method, basically, necessary values such as $P_x$ and $P_y$ can be obtained as analytically expressed parameters, though detailed equations are different between transmission light measurement and reflection light measurement.

It must be assumed to handle the interactive terms as undefined coefficients, but the solution can be obtained by measurements at a plurality of wavelengths.

This method is based on the principle with completely mathematically guaranteed strictness and therefore is suitable to handle a complex problem. Hence, the method of the present invention is suitable for measurement of the above-mentioned substances that are inhomogeneous and exhibit strong scattering.

The above-described method uses the fact that the light amount becomes the sum of exponential functions because of the inhomogeneous structure. The known prior arts described above claim that the measurement result is corrected for a homogeneous phase. However, this method claims that for an inhomogeneous phase, a correct value can be calculated from the combined equations.

As described above, as a characteristic feature of the method, light is made incident into an inhomogeneous medium, the intensity of light that emerges from the inhomogeneous medium is detected, the detected intensity of the light depends on the physical quantity of the inhomogeneous medium, and the physical quantity of the inhomogeneous medium is determined on the basis of a function represented by the linear sum of exponential functions of the penetration depth with e as a base and/or an expression derived from the function. In this case, optical analysis for the inhomogeneous medium can be accurately performed.

According to the method, when the inhomogeneous medium is a polyphase or polyphase separate structure such as an inhomogeneous medium or a mixture, the phase components in each part can be separated and independently calculated using the method.

When the inhomogeneous medium is formed from multiple divisional parts, simultaneous equations containing parameters in number corresponding to the number of part types are contracted, and the method can be applied to the analysis method for two parts X and Y.

As has been described above, according to the method of the embodiment, an optical analysis method of determining a physical quantity of a medium from an intensity of light transmitted through or reflected by the medium, the medium being an absorbent and scattering medium containing a plurality of parts of different medium having different optical characteristics, is characterized by comprising the first step of making light having a known intensity incident on the medium; the second step of measuring the intensity of the light that emerges from the medium; the third step of storing light intensity numerical values; the fourth step of deriving a coefficient necessary for arithmetic operation by erasing or avoiding influence of inhomogeneous light scattering by arithmetic operation for a combination of the numerical values; the fifth step of storing the obtained coefficient; and the sixth step of performing linear algebraic operation for optimization in a wavelength range using the light intensity measurement values at a plurality of wavelengths, wherein the function used for the arithmetic operation is defined as simultaneous differential equations that describe light amount re-distribution by light scattering between the parts, i.e., a basic system that expresses light re-distribution given by $$dx/dt = -ax + by$$
$$dy/dt = cx - dy$$

where assuming that the medium contains two, first and second parts, x is a light intensity in the first part, y is a light intensity in the second part, $\underline{a}$ is a loss coefficient by absorption and scattering in the first part, b is a coefficient of a component of scattered light in the second part, which mixes into the first part, c is a coefficient of a component of scattered light in the first part, which mixes into the second part, d is a loss coefficient by absorption and scattering in the second part, and t is a penetration depth of the light into the inhomogeneous medium, and as a linear sum of exponential functions for t, which uses e as a base and is given by $$I = x + y = \frac{1}{2}(e^{-\alpha t} + e^{-\beta t})$$

which represents a light-intensity I standardized as a sum of general solutions x and y corresponding to the basic system, thereby derivatively calculating the physical quantity from the light amount measurement values on the basis of a relationship between the coefficients (a, b, c, d) and unknowns ($\alpha$, $\beta$). According to this method, the physical quantity of the inhomogeneous medium can be accurately analyzed.

Preferably, the emerging light is light reflected by the inhomogeneous medium, and the function related to the light amount of the reflected light is a linear sum of $(\alpha+\beta)/\alpha\beta$ and $1/(\alpha+\beta)$.

The physical quantity is preferably an absorption coefficient of the inhomogeneous medium, a scattering coefficient of the inhomogeneous medium, or a concentration of a predetermined component in the inhomogeneous medium.

The method preferably comprises using a method of facilitating the arithmetic operation using a fact that inter-scattering coefficients that define the light amount re-distribution often equal.

What is claimed is:

1. An optical analysis method of determining a physical quantity of a medium from an intensity of light transmitted through or reflected by the medium, the medium being an absorbent and scattering medium containing a plurality of parts having different optical characteristics, characterized by comprising:

the first step of making light having a known intensity incident on the medium; the second step of measuring the intensity of the light that emerges from the medium; the third step of storing light intensity numerical values; the fourth step of deriving a coefficient necessary for arithmetic operation by erasing or avoiding influence of inhomogeneous light scattering by arithmetic operation for a combination of the numerical values; the fifth step of storing the obtained coefficient; and the sixth step of performing linear algebraic operation for optimization in a wavelength range using the light intensity measurement values at a plurality of wavelengths, wherein the function used for the arithmetic operation is defined as simultaneous differential equations that describe light amount re-distribution by light scattering between the parts, i.e., a basic system that expresses light re-distribution given by $dx/dt = -ax + by$ $dy/dt = cx - dy$ where assuming that the medium contains two, first and second parts, x is a light intensity in the first part, y is a light intensity in the second part, a is a loss coefficient by absorption and scattering in the first part, b is a coefficient of a component of scattered light in the second part, which mixes into the first part, c is a coefficient of a component of scattered light in the first part, which mixes into the second part, d is a loss coefficient by absorption and scattering in the second part, and t is a penetration depth of the light into the inhomogeneous medium, and as a linear sum of exponential functions for t, which uses e as a base and is given by $$I = x + y = \frac{1}{2}(e^{-\alpha t} + e^{-\beta t})$$

which represents a light intensity I standardized as a sum of general solutions x and y corresponding to the basic system, thereby derivatively calculating the physical quantity from the light amount measurement values on the basis of a relationship between the coefficients (a, b, c, d) and unknowns ($\alpha$, $\beta$).

2. An optical analysis method for an inhomogeneous medium according to claim 1, characterized in that the emerging light is light reflected by the inhomogeneous medium, and the function related to a light amount of the reflected light is a linear sum of $(\alpha+\beta)/\alpha\beta$ and $1/(\alpha+\beta)$.

3. An optical analysis method for an inhomogeneous medium according to claim 1, characterized in that the physical quantity is an absorption coefficient of the inhomogeneous medium, a scattering coefficient of the inhomogeneous medium, or a concentration of a predetermined component in the inhomogeneous medium.

4. An optical analysis method for an inhomogeneous medium according to claim 1, characterized by comprising using a method of facilitating arithmetic operation using a fact that interscattering coefficients that define the light amount re-distribution often equal.

* * * * *